(12) United States Patent
Batz-Sohn et al.

(10) Patent No.: US 6,472,549 B1
(45) Date of Patent: Oct. 29, 2002

(54) PROCESS FOR THE PRODUCTION OF PROPYL SILANES FUNCTIONALIZED IN 3-POSITION

(75) Inventors: Christoph Batz-Sohn, Hanau (DE); Peter Panster, Rodenbach (DE); Rudolf Michel, Freigericht (DE); Michael Albert, Neustadt (DE); Ivo Vryens, Schoten (BE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 10/060,287

(22) Filed: Feb. 1, 2002

(30) Foreign Application Priority Data

Feb. 3, 2001 (DE) .......................................... 101 04 966

(51) Int. Cl.$^7$ .............................. C07F 7/08; C07F 7/10
(52) U.S. Cl. ...................... 556/479; 532/414; 532/415; 532/427; 532/413; 532/459
(58) Field of Search ................. 556/479, 415, 556/414, 427, 413, 459

(56) References Cited

U.S. PATENT DOCUMENTS

| | | |
|---|---|---|
| 2,637,738 A | 5/1953 | Wagner |
| 4,292,433 A | 9/1981 | Koga et al. |
| 4,292,434 A | 9/1981 | Lindner et al. ............. 556/479 |
| 5,177,236 A * | 1/1993 | Seiler et al. ................. 556/479 |
| 6,153,782 A * | 11/2000 | Krauter et al. .............. 556/479 |
| 6,191,297 B1 * | 2/2001 | Batz-Sohn et al. ......... 556/479 |

FOREIGN PATENT DOCUMENTS

| | | |
|---|---|---|
| CZ | 176910 | 2/1979 |
| DE | 1 165 028 | 3/1964 |
| DE | 1 187 240 | 2/1965 |
| DE | 2 012 229 | 9/1971 |
| DE | 28 15 316 | 7/1979 |
| DE | 28 51 456 | 6/1980 |
| EP | 0 152 803 A2 | 8/1985 |
| EP | 0 963 993 A2 | 12/1999 |

OTHER PUBLICATIONS

European Search Report issued for corresponding European Appln. No. EP 02 00 0682 dated May 13, 2002.
Database WPI Section Ch, Week 198103, Derwent Publications Ltd., London, GB; Class E11, AN 1981–03066D XP002197301 & JP 55 145693 A (CHISSO CORP), Nov. 13, 1980.

* cited by examiner

*Primary Examiner*—Paul F. Shaver
(74) *Attorney, Agent, or Firm*—Smith, Gambrell & Russell, LLP

(57) ABSTRACT

Propyl silanes functionalized in 3-position are produced by catalytically reacting allyl compounds of the formula $H_2C=CH-CH_2X$ with silanes of the formula $R^2R^3R^4SiH$ and using a 3- to 100-fold excess of silane.

12 Claims, 3 Drawing Sheets

PROCESS FOR THE PRODUCTION OF PROPYL SILANES FUNCTIONALIZED IN 3-POSITION

INTRODUCTION AND BACKGROUND

The present invention relates to a process for the production of 3-functionalized propyl silanes.

It is known, that hydrogen silanes can be reacted with, for example, allyl chloride in the presence of homogeneous or heterogeneous platinum catalysts to produce 3-chloropropyl silanes. This reaction is generally known as hydrosilylation (see for example equation I).

$$Cl-CH_2-CH=CH_2+HSiCl_3 \rightarrow Cl-CH_2-CH_2-CH_2-SiCl_3 \quad (I)$$

If soluble platinum compounds, in the simplest case, for example, $H_2PtCl_6 \times 6\ H_2O$, are used (cf. DE-OS 28 51 456, CS-PS 176 910, U.S. Pat. No. 4,292,433, U.S. Pat. No. 4,292,434, DE-AS 11 87 240, DE-PS 11 65 028) this is called homogenous hydrosilylation. With heterogeneous hydrosilylation, elemental platinum or platinum compounds on a carrier are used (cf. U.S. Pat. No. 2,637,738, DE-PS 20 12 229, DE-PS 28 15 316).

Furthermore, it is known that when reacting, for example, allyl chloride with hydrogen silanes to produce 3-chloropropyl silanes, some of the allyl chloride used reacts with the hydrogen silane in a secondary reaction producing propene and the chlorosilane corresponding to the particular hydrogen silane (see for example equation II).

$$Cl-CH_2-CH=CH_2+HSiCl_3 \rightarrow CH_3-CH=CH_2+SiCl_4 \quad (II)$$

Thus, when reacting allyl chloride with trichlorosilane, for example, 25–30 mol % of the allyl chloride attaining reaction is converted by this secondary reaction into propene. This produces an equivalent quantity of silicon tetrachloride.

The mol ratio of chloropropylsilane to silicon tetrachloride produced is a measure of the selectivity of the reaction and typically achieves values of 2.33:1 (70% yield in relation to allyl chloride) and 3:1 (75% yield).

Furthermore it is known that the formation of propene can be reduced by a special reaction method using pressure apparatus. The result of this method is that the propene further reacts quantitatively with the hydrogen silane to produce propyl silanes. Even with the reactions carried out in the usual way, under normal pressure, a considerable quantity of the propene originating from the secondary reaction is converted to the corresponding propyl silanes in a further secondary reaction with hydrogen silane (cf. also DE 34 04 703 C) (see for example equation 3).

$$CH_3-CH=CH_2+HSiCl_3 \rightarrow CH_3-CH_2-CH_2-SiCl_3 \quad (III)$$

Thus, for example, a heterogeneous catalytic reaction in a commercial apparatus of allyl chloride and trichlorosilane in an acid filled with platinated active carbon produces up to 230 kg propyl trichlorosilane per 1000 kg 3-chloropropyl trichlorosilane. This requires an excess of approx. 28% trichlorosilane in relation to the quantity of trichlorosilane incorporated into the end product (cf. also DE 41 19 944 A1).

The known processes have the disadvantage that, firstly, there is a need for additional hydrogen silane and secondly, the unwanted propyl silanes are not easy to separate off. In addition to this, there are few applications for these compounds, which must therefore be disposed of at great cost.

An object of the present invention is therefore to find a process for the production of 3-position functionalized propyl silanes, which does not have these disadvantages.

SUMMARY OF THE INVENTION

The above and other objects of the invention can be achieved by a process for the production of 3-functionalized propyl silanes by the addition of allyl compounds of the general formula I $$H_2C=CH-CH_2X \quad (I)$$

wherein X can be Cl, Br, I, F, CN, SCN, SH, SR, OH, $NRR^1$ and OR, and R and $R^1$, both independently of each other, mean $(C_1-C_6)$alkyl or $(C_3-C_7)$alkyl, to silanes of the formula II $$R^2R^3R^4SiH \quad (II),$$

wherein $R^2$, $R^3$, $R^4$, all independently of each other, are hydrogen, halogen, $(C_1-C_6)$alkyl, $(C_1-C_6)$haloalkyl, $(C_3-C_6)$allyl, $(C_1-C_4)$alkoxy, phenyl, aryl or aralkyl, at reaction temperatures of 0° C. to 200° C. and pressures of 800 mbar to 25 bar and in the presence of a platinum catalyst, characterised in that the silane (II) used is brought into contact with the catalyst in a 3- to 100-fold molar excess in relation to the propene compound (I).

Surprisingly, it is found that the formation of by-products is suppressed if large excesses of hydrogen silane are present on the catalyst. Then, in the reaction of allyl chloride with trichlorosilane for example, the selectivity normally achieved of 74% Cl-PTS yield in relation to allyl chloride can be increased to 85%. At the same time, the quantity of the by-product propyl trichlorosilane formed is reduced by 50% and the need for trichlorosilane educts by 20%, and allyl chloride by 12%.

A halogen, in particular chlorine, can preferably represent X.

The process can be carried out at normal pressure, excess pressure or reduced pressure. Pressures of 800 mbar to 10 bar are preferred. A pressure of 800 mbar to 6 bar is particularly suitable.

BRIEF DESCRIPTION OF DRAWINGS

The present invention will be further understood with reference to the accompanying drawings, wherein.

DETAILED DESCRIPTION OF INVENTION

The process according to the invention can usefully be carried out in such a way that the allyl compound and the hydrogen silane used in a large stoichiometric excess, are reacted together with the catalyst in a suitable container at temperatures of 0° C. to 300° C., preferably 25° C. to 200° C., until all of the allyl compound has been converted.

The large stoichiometric excesses according to the invention of silanes of type (II) can be realized technologically in various ways on contact with the platinum catalyst.

Firstly, the excess of component II can be set directly on the catalyst by mixing components I and II.

Secondly, both components of the addition reaction can be brought into contact with the catalyst in a suitable reaction container and thus reacted with it, and any desired ratio of the components can be set i.e. also the large excesses of the silane component according to the invention. The reaction container can be a discontinuously operated stirred tank or a continuously operated tube reactor filled with catalyst.

Thirdly, the excess of component (II) on the catalyst can be achieved by using a cascade of at least two, preferably two to ten, tube reactors, dosing proportionate quantities of component (I) between the reactors and reacting it in the following reactor in each case. This embodiment of the invention is illustrated in FIG. 1.

Figure 1:
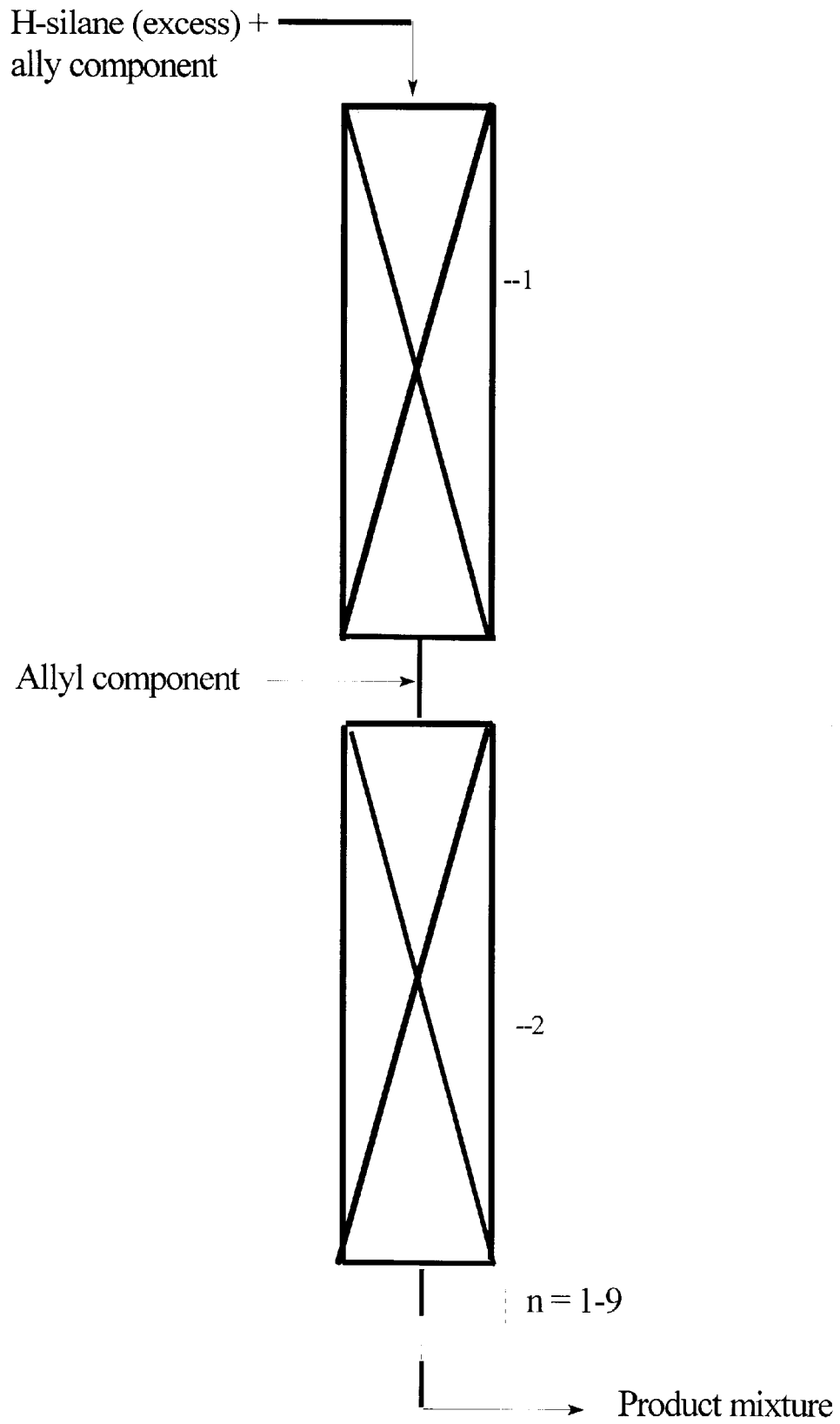
FIG. 1 is a schematic diagram of apparatus used in accordance with one embodiment of the present invention.

According to this embodiment of the invention as shown in FIG. 1, the excesses according to the invention of the silane component can be achieved in continuously operated, catalyst-filled tube reactors, by linking together at least two, preferably two to ten tube reactors of the same type, one after the other, in such a way that the first reactor (1) as is fed with a mixture that contains a very large excess of the silane component, and the allyl component is completely reacted off in this first reactor. The product mixture discharged from the first reactor is then mixed with a small portion of the allyl component, so that a large excess of the silane component is once again achieved; the new mixture thus formed is fed into the second reactor (2). This process can be used for all tube reactors linked together one after the other and filled with catalyst, by dosing the allyl component between the reactors. Thus the excess of the silane component according to the invention is always produced on the catalyst.

Figure 2:
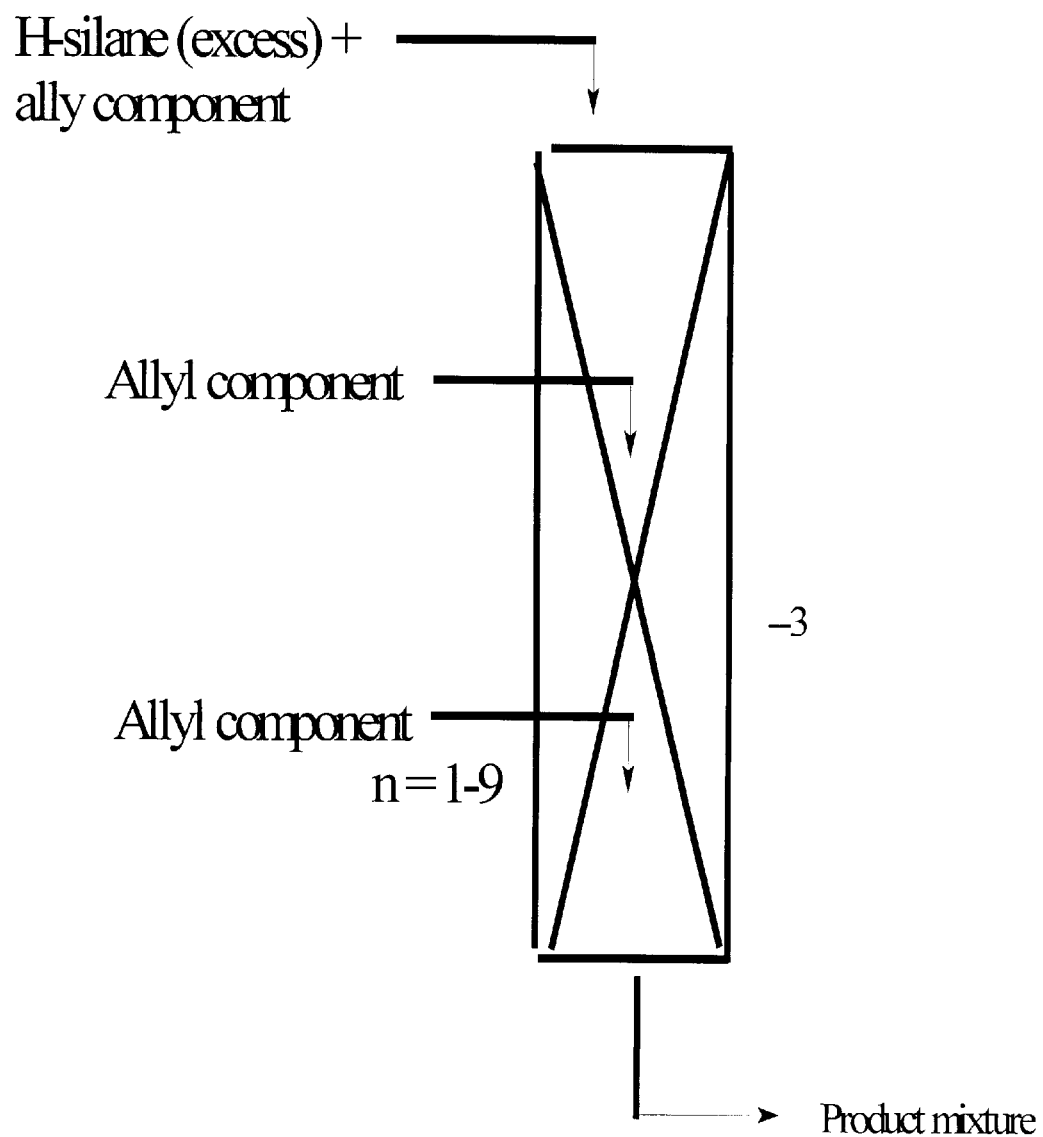
FIG. 2 is a schematic diagram of apparatus used in accordance with a second embodiment of the present invention.

In a further embodiment of the invention, as shown in FIG. 2, the cascade can be replaced by a single tube reactor (3), and the deficit component (I) is dosed subsequently through at least one, preferably one to nine, tubes fitted to the side of the reactor. Accordingly, throughout a single tube reactor, one to nine additional dosing points for the allyl component can be used to add a suitably small portion of the allyl component. Thus a large excess of silane can always be achieved locally on the catalyst.

Figure 3:
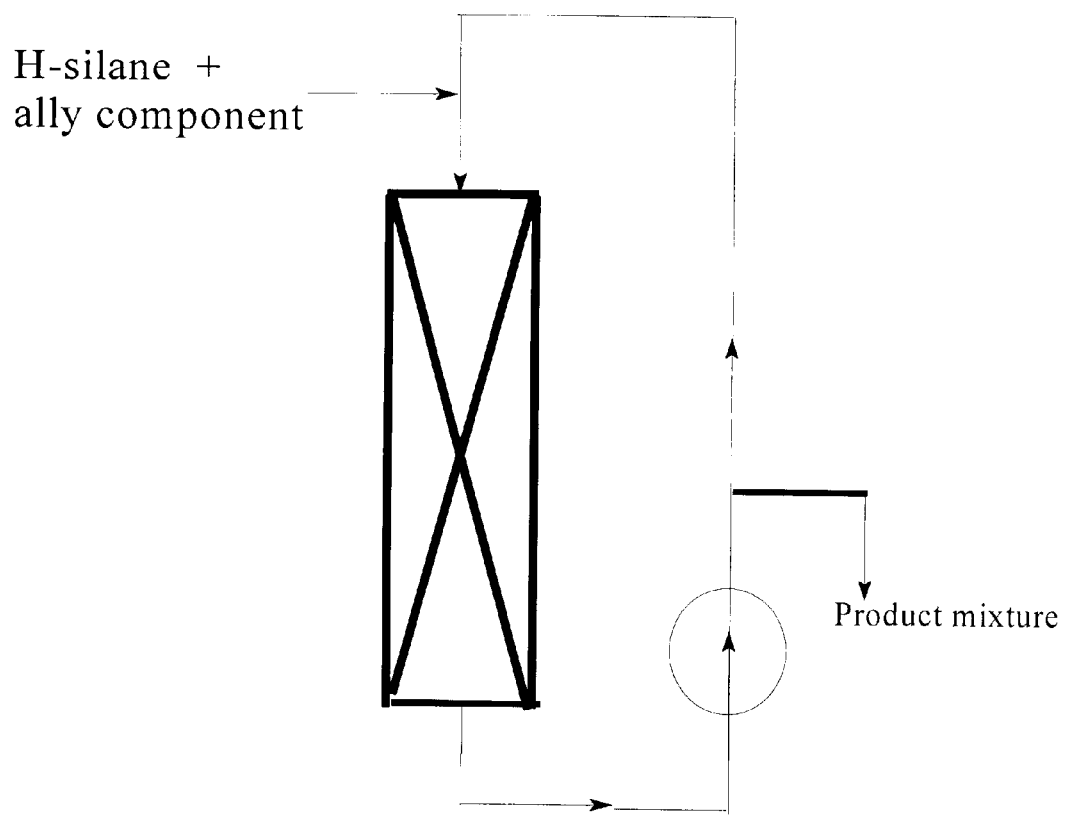
FIG. 3 is a schematic diagram of apparatus used in accordance with a third embodiment of the present invention.

In a further embodiment of the invention, as shown in FIG. 3, the excess of silane on the catalyst can be increased by re-circulating the majority of the substance stream passing through the reactor (4) to the top of the reactor and removing from the circulation only that quantity of product mixture that is dosed on the other side as an educt mixture. At the same time, the excess of the silane component, in relation to the allyl component, set in the educt stream can be multiplied depending on the ratio of circulation quantity to educt quantity set, as the allyl component is reacted off as it passes through the tube reactor.

In this way, with a 3:1 excess of silane in the educt stream and a suitable choice of parameters for the catalyst, silane excesses greater than 15:1 can be achieved.

The stated processes according to the invention for achieving higher excesses of the silane component on contact with the catalyst can also be used in combination.

The silanes that can be used according to the invention as starting components comprise silanes of structural type II $$R^2R^3R^4SiH \quad (II)$$

wherein $R^2$, $R^3$ and $R^4$, all independently of each other, can be hydrogen, halogen, $(C_1-C_6)$alkyl, $(C_1-C_6)$alkoxy, $(C_1-C_6)$haloalkyl, $(C_3-C_6)$allyl, phenyl, aryl or aralkyl.

Silanes such as trichlorosilane, or mixed substituted silanes, such as for example, methyl-, ethyl-, propylhydrogen dichlorosilane or dimethylhydrogen chlorosilane are preferred.

The platinum catalyst can be used at any oxidation stage. Catalysis can take place both homogeneously or heterogeneously. With heterogeneous catalysis, the catalytically active platinum compound can be applied to a carrier (cf. U.S. Pat. No. 2,637,738, DE-PS 20 12 229, DE-PS 29 15 316). Thus, such catalysts are well known in the art and this prior art is relied on and incorporated herein by reference.

The catalyst can be used both in stoichiometric and in catalytic quantities, for example of 0.1 to 10000 ppm, preferably 10 to 500 ppm, in relation to the allyl compound. A heterogenous catalyst is preferred.

Here, selectivity is understood to mean the molar ratio of the desired product 3-chloropropyl trichlorosilane (Cl-PTS) to silicon tetrachloride.

The examples according to the invention show, by the selectivities achieved and yields of 3-chloropropyl trichlorosilane, the extent of the advantages offered by the process according to the invention.

EXAMPLE 1

Reference Example

First, 1 1 3-chloropropyl trichlorosilane is dosed into a 40 cm tube reactor with a volume of 150 ml, which can be heated and which is filled with approx. 100 g platinated, granulated active carbon (1 wt. % platinum). 200 ml per hour of a mixture of trichlorosilane and allyl chloride (molar ratio 1.43:1) is then dosed at approximately 90° C. and a pressure of 2 bar. After 5 hours a sample is taken from the reactor outlet, cooled and analyzed. The following product composition results:

| | | |
|---|---|---|
| 6.75 | wt. % | trichlorosilane (TCS) |
| — | wt. % | allyl chloride (ACl) |
| 19.31 | wt. % | silicon tetrachloride (STC) |
| 19.26 | wt. % | propyl trichlorosilane (PTS) |
| 54.68 | wt. % | 3-chloropropyl trichlorosilane (Cl-PTS). |

The selectivity of the reaction in relation to the quantities of substance is thus 2.27:1. This is equivalent to a yield of 69.4% 3-chloropropyl trichlorosilane in relation to allyl chloride.

EXAMPLE 2

As in example 1, except that the molar ratio of trichlorosilane to allyl chloride is 2.8:1. After analysis the following product composition results:

| | | |
|---|---|---|
| 43.22 | wt. % | trichlorosilane (TCS) |
| — | wt. % | allyl chloride (ACl) |
| 9.69 | wt. % | silicon tetrachloride (STC) |
| 10.14 | wt. % | propyl trichlorosilane (PTS) |
| 39.96 | wt. % | 3-chloropropyl trichlorosilane (Cl-PTS). |

The selectivity of the reaction in relation to the quantities of substance is thus 3.06:1. This is equivalent to a yield of 75.4% 3-chloropropyl trichlorosilane in relation to allyl chloride.

EXAMPLE 3

As in example 1, except that the majority of the product mixture discharged from the bottom of the reactor is re-circulated to the top of the reactor by a pump. At the same time, the ratio of the circulation volume to the educt volume is set at 13:1. The mass flow balance thus produces a molar ratio of trichlorosilane to allyl chloride of 3:1 at the top of the reactor. With this method a sample of the product mixture is taken and analyzed only after 97 h. The following product composition results:

| | | |
|---|---|---|
| 7.82 | wt. % | trichlorosilane (TCS) |
| 0.19 | wt. % | allyl chloride (ACl) |
| 15.67 | wt. % | silicon tetrachloride (STC) |
| 16.39 | wt. % | propyl trichlorosilane (PTS) |
| 59.13 | wt. % | 3-chloropropyl trichlorosilane (Cl-PTS). |

The selectivity of the reaction in relation to the quantities of substance is thus 3.02:1. This is equivalent to a yield of 75.1% 3-chloropropyl trichlorosilane in relation to allyl chloride.

EXAMPLE 4

As in example 3, except that the molar ratio of the educts trichlorosilane and allyl chloride is 2.8:1. The mass flow balance thus produces a molar ratio of trichlorosilane to allyl chloride of 14:1 at the top of the reactor. The following product composition results:

| | | |
|---|---|---|
| 42.41 | wt. % | trichlorosilane (TCS) |
| 0.68 | wt. % | allyl chloride (ACl) |
| 7.80 | wt. % | silicon tetrachloride (STC) |
| 7.52 | wt. % | propyl trichlorosilane (PTS) |
| 41.35 | wt. % | 3-chloropropyl trichlorosilane (Cl-PTS). |

The selectivity of the reaction in relation to the quantities of substance is thus 4.25:1. This is equivalent to a yield of 81.0% 3-chloropropyl trichlorosilane in relation to allyl chloride.

EXAMPLE 5

As example 3, except that the molar ratio of the educts trichlorosilane and allyl chloride is 2.0:1. Also, the ratio of circulation volume to educt volume is 30:1. The mass flow balance thus produces a molar ratio of trichlorosilane to allyl chloride of 25:1 at the top of the reactor. The following product composition results:

| | | |
|---|---|---|
| 30.71 | wt. % | trichlorosilane (TCS) |
| 0.78 | wt. % | allyl chloride (Al) |
| 7.51 | wt. % | silicone tetrachloride (STC) |
| 8.05 | wt. % | propyl trichlorosilane (PTS) |
| 52.96 | wt. % | 3-chloropropyl trichlorosilane (Cl-PTS). |

The selectivity of the reaction in relation to the quantities of substance is thus 5.65:1. This is equivalent to a yield of 85% 3-chloropropyl trichlorosilane in relation to allyl chloride.

EXAMPLE 6

As in example 3, except that half of the total quantity of allyl chloride dosed is additionally fed into the reactor half way up. The other half is dosed at the top of the reactor with the TCS, as in example 3. This results in a molar excess of TCS on the catalyst of approximately 14:1. The following product composition results:

| | | |
|---|---|---|
| 33.69 | wt. % | trichlorosilane (TCS) |
| 0.68 | wt. % | allyl chloride (ACl) |
| 10.36 | wt. % | silicon tetrachloride (STC) |
| 10.47 | wt. % | propyl trichlorosilane (PTS) |
| 44.80 | wt. % | 3-chloropropyl trichlorosilane (Cl-PTS). |

The selectivity of the reaction in relation to the quantities of substance is thus 3.5:1. This is equivalent to a yield of 78% 3-chloropropyl trichlorosilane in relation to allyl chloride.

EXAMPLE 7

As in example 2, except that the reaction is carried out in two reactors linked together one after the other each with a volume of 1.71 charged with 250 ml of the mixture. The molar excess of TCS at the intake of the first reactor is thus approximately 2.8:1. The following product composition results:

| | | |
|---|---|---|
| 46.56 | wt. % | trichlorosilane (TCS) |
| 0.00 | wt. % | allyl chloride (ACl) |
| 8.92 | wt. % | silicone tetrachloride (STC) |
| 9.34 | wt. % | propyl trichlorosilane (PTS) |
| 35.18 | wt. % | 3-chloropropyl trichlorosilane (Cl-PTS). |

The selectivity of the reaction in relation to the quantities of substance is thus 3.1:1. This is equivalent to a yield of 76% 3-chloropropyl trichlorosilane in relation to allyl chloride.

EXAMPLE 8

As in example 7, except that half of the total quantity of allyl chloride dosed is fed in before the second reactor. The other half is fed into the first reactor with the TCS as in example 7. The molar excess of TCS at the intake is therefore approx. 5.6:1 for the first and approx. 4.4:1 for the second reactor. The following product composition results:

| | | |
|---|---|---|
| 47.55 | wt. % | trichlorosilane (TCS) |
| 0.00 | wt. % | allyl chloride (ACl) |
| 7.59 | wt. % | silicon tetrachloride (STC) |
| 8.03 | wt. % | propyl trichlorosilane (PTS) |
| 36.83 | wt. % | 3-chloropropyl trichlorosilane (Cl-PTS). |

The selectivity of the reaction in relation to the quantities of substance is thus 3.6:1. This is equivalent to a yield of 78% 3-chloropropyl trichlorosilane in relation to allyl chloride.

EXAMPLE 9

As in example 8, except that the reaction is carried out in three reactors linked together one after the other, each with a volume of 1.71. A third of the total quantity of allyl chloride dosed is fed in before the second and the third reactor, the other third is added to the first reactor with the TCS. The molar excess of TCS at the intake is thus approximately 8.4:1 for the first reactor, 7.3:1 for the second reactor and 6.1:1 for the third reactor. The following product composition results:

| | | |
|---|---|---|
| 48.14 | wt. % | trichlorosilane (TCS) |
| 0.00 | wt. % | allyl chloride (ACl) |
| 6.89 | wt. % | silicon tetrachloride (STC) |
| 7.26 | wt. % | propyl trichlorosilane (PTS) |
| 37.71 | wt. % | 3-chloropropyl trichlorosilane (Cl-PTS). |

The selectivity of the reaction in relation to the quantities of substance is thus 4.0:1. This is equivalent to a yield of 80% 3-chloropropyl trichlorosilane in relation to allyl chloride.

EXAMPLE 10

As in example 9, except that reactors with a volume of 0.8 l each are used and the molar ratio of trichlorosilane to allyl chloride is 3.4:1. The majority of the product mixture discharged from the bottom of the third reactor is re-circulated to the intake of the first reactor by a pump, and at the same time the ratio of circulation volume to educt volume is set at 10:1. The mass flow balance produces a molar excess of TCS of approx. 57:1 at the intake of the first reactor, approx. 55:1 at the intake of the second reactor and approx. 54:1 at the intake of the third reactor. The following product composition results:

| | | |
|---|---|---|
| 57.55 | wt. % | trichlorosilane (TCS) |
| 0.16 | wt. % | allyl chloride (ACl) |
| 3.77 | wt. % | silicon tetrachloride (STC) |
| 3.94 | wt. % | propyl trichlorosilane (PTS) |
| 34.58 | wt. % | 3-chloropropyl trichlorosilane (Cl-PTS). |

The selectivity of the reaction in relation to the quantities of substance is thus 5.7:1. This is equivalent to a yield of 85% 3-chloropropyl trichlorosilane in relation to allyl chloride.

EXAMPLE 11

As in example 7, except that the molar ratio of trichlorosilane to allyl chloride is 3.4:1 and the majority of the product mixture discharged from the bottom of the second reactor is re-circulated to the intake of the first reactor by a pump. At the same time, the ratio of circulation volume to educt volume is set at 10:1. The mass flow balance produces a molar excess of TCS of approx. 23:1 at the intake of the first reactor. The following product composition results:

| | | |
|---|---|---|
| 56.79 | wt. % | trichlorosilane (TCS) |
| 0.03 | wt. % | allyl chloride (ACl) |
| 4.42 | wt. % | silicon tetrachloride (STC) |
| 4.62 | wt. % | propyl trichlorosilane (PTS) |
| 34.14 | wt. % | 3-chloropropyl trichlorosilane (Cl-PTS). |

The selectivity of the reaction in relation to the quantities of substance is thus 5.1:1. This is equivalent to a yield of 84% 3-chloropropyl trichlorosilane in relation to allyl chloride.

EXAMPLE 12

As example 4, except that the reactor volume is 4 m$^3$. The molar ratio of trichlorosilane to allyl chloride is 1.8:1 and the reactor is charged with 1180 l of the mixture. The ratio of circulation volume to educt volume is set at 5.5:1. The mass flow balance produces a molar excess of TCS of approx. 4.5:1 at the reactor intake. The following product composition results:

| | | |
|---|---|---|
| 26.15 | wt. % | trichlorosilane (TCS) |
| 0.11 | wt. % | allylchloride (ACl) |
| 11.13 | wt. % | silicon tetrachloride (STC) |
| 11.63 | wt. % | propyl trichlorosilane (PTS) |
| 50.98 | wt. % | 3-chloropropyl trichlorosilane (Cl-PTS). |

The selectivity of the reaction in relation to the quantities of substance is thus 3.5:1. This is equivalent to a yield of 78% 3-chloropropyl trichlorosilane in relation to allyl chloride.

EXAMPLE 13

As in example 8, except that the molar ratio of trichlorosilane to allyl chloride is 2.0:1 and the majority of the product mixture discharged from the bottom of the second reactor is re-circulated to the intake of the first reactor by a pump. At the same time, the ratio of circulation volume to educt volume is set at 11.5:1. The mass flow balance produces a molar excess of TCS of approx. 21:1 at the intake of the first reactor and 20:1 at the intake of the second reactor. The following product composition results:

| | | |
|---|---|---|
| 33.27 | wt. % | trichlorosilane (TCS) |
| 0.09 | wt. % | allyl chloride (ACl) |
| 7.30 | wt. % | silicon tetrachloride (STC) |
| 7.62 | wt. % | propyl trichlorosilane (PTS) |
| 51.72 | wt. % | 3-chloropropyl trichlorosilane (Cl-PTS). |

The selectivity of the reaction in relation to the quantities of substance is thus 4.8:1. This is equivalent to a yield of 83% 3-chloropropyl trichlorosilane in relation to allyl chloride.

Further variations and modifications of the foregoing will be apparent to those skilled in the art and one intended to be encompassed by the claims appended hereto.

German priority application 101 04 966.8 is relied on and incorporated herein by reference.

We claim:

1. A process for the production of a 3-functionalized propyl silane comprising:

adding an allyl compound of formula I

$$H_2C=CH-CH_2X \qquad (I),$$

wherein X is Cl, Br, I, F, CN, SCN, SH, SR, OH, NRR$^1$ or OR and R and R$^1$, both independently of each other, mean (C$_1$–C$_6$)alkyl or (C$_3$–C$_7$)alkyl, to a silanes of formula II

$$R^2R^3R^4SiH \qquad (II)$$

wherein R$^2$, R$^3$, R$^4$, all independently of each other, are hydrogen, halogen, (C$_1$–C$_6$)alkyl, (C$_1$–C$_6$)haloalkyl, (C$_3$–C$_6$)allyl, (C$_1$–C$_4$)alkoxy, phenyl, aryl or aralkyl, at a reaction temperature of 0° C. to 200° C. and a pressure of 800 mbar to 25 bar and in the presence of a platinum catalyst, wherein the silane (II) is brought into contact with the catalyst in a 3- to 100-fold molar excess in relation to the compound (I) to form an addition reaction.

2. The process according to claim 1, wherein the silane is a member selected from the group consisting of trichlorosilane, methylhydrogen dichlorosilane, ethylhydrogen dichlorosilane, propylhydrogen dichlorosilane and dimethylhydrogen chlorosilane.

3. The process according to claim 1, wherein the addition reaction is carried out in a discontinuously operated stirred tank.

4. The process according to claim 1, wherein the addition reaction is carried out in a continuously operated tube reactor filled with catalyst.

5. The process according to claim 1, wherein excess of component (II) on the catalyst is set directly by mixing component (I) and component (II).

6. The process according to claim 1, further comprising producing an excess of component (II) on the catalyst by re-circulating a majority of product mixture discharged to the top of a continuously operated tube reactor.

7. The process according to claim 1, further comprising producing an excess of component (II) on the catalyst dosing proportionate quantities of component (I) between reaction in a cascade of at least two tube reactors and reacting in a following reactor.

8. The process according to claim 1, wherein a single tube reactor is used, the component (I) being dosed subsequently through up to nine tubes fitted to the side of the reactor.

9. The process according to claim 1, wherein catalyst concentration is set at 0.1 to 10000 ppm in relation to the allyl compound.

10. The process according to claim 1, wherein the reaction is carried out at pressures of 800 mbar to 10 bar.

11. The process according to claim 1, wherein X is Cl.

12. The process according to claim 1, wherein the catalyst is heterogenous.

* * * * *